(12) United States Patent
Heyrani-Nobari et al.

(10) Patent No.: US 11,416,945 B2
(45) Date of Patent: Aug. 16, 2022

(54) METHODS AND SYSTEMS FOR BEHAVIOR SIGNAL GENERATION AND PROCESSING

(71) Applicant: Optum Services (Ireland) Limited, Dublin (IE)

(72) Inventors: Ghasem Heyrani-Nobari, Dublin (IE); Jose Antonio Sierra Padilla, Rathmines (ES)

(73) Assignee: Optum Services (Ireland) Limited, Dublin (IE)

( * ) Notice: Subject to any disclaimer, the term of this patent is extended or adjusted under 35 U.S.C. 154(b) by 281 days.

(21) Appl. No.: 16/747,991

(22) Filed: Jan. 21, 2020

(65) Prior Publication Data
US 2021/0224918 A1    Jul. 22, 2021

(51) Int. Cl.
| | |
|---|---|
| *G06Q 40/08* | (2012.01) |
| *G16H 10/60* | (2018.01) |
| *G06N 20/10* | (2019.01) |
| *G06K 9/62* | (2022.01) |
| *G06Q 10/10* | (2012.01) |

(52) U.S. Cl.
CPC .......... *G06Q 40/08* (2013.01); *G06K 9/6226* (2013.01); *G06N 20/10* (2019.01); *G06Q 10/10* (2013.01); *G16H 10/60* (2018.01)

(58) Field of Classification Search
CPC ............................... G06Q 40/08; G16H 10/60
USPC .......................................................... 705/4
See application file for complete search history.

(56) References Cited

U.S. PATENT DOCUMENTS

| | | | | |
|---|---|---|---|---|
| 5,822,741 | A  * | 10/1998 | Fischthal | G06Q 40/08 705/31 |
| 8,639,522 | B2 * | 1/2014 | Pathria | G06Q 40/02 705/2 |
| 9,646,258 | B2 | 5/2017 | Enck et al. | |
| 10,389,739 | B2 | 8/2019 | Solotorevsky | |
| 2014/0149128 | A1 | 5/2014 | Getchius | |
| 2014/0278490 | A1 | 9/2014 | Namazifar et al. | |

(Continued)

OTHER PUBLICATIONS

Ali, Mohammed et al. "TimeCluster: Dimension Reduction Applied To Temporal Data For Visual Analytics," The Visual Computer, vol. 35, No. 6-8, May 9, 2019, pp. 1013-1026. [Retrieved From The Internet Apr. 7, 2020] <https://link.springer.com/article/10.1007/s00371-019-01673-y>.

(Continued)

*Primary Examiner* — Robert R Niquette
(74) *Attorney, Agent, or Firm* — Alston & Bird LLP

(57) ABSTRACT

Instances of claim data are received by an apparatus. Each instance of claim data corresponds to an entity. A claim vector is generated for each instance of claim data. The claim vector is added to a group of claim vectors that all correspond to a same entity. Each group of claim vectors is aggregated to generate an entity vector corresponding to the entity. Based at least in part on the entity vector and (a) an entity profile corresponding to the corresponding entity or (b) an entity cluster with which the entity is associated, at least one behavior signal value is determined for the entity. A behavior signal is amended to include the behavior signal value. The behavior signal comprises at least two behavior signal values. Each of the behavior signal values are associated with a different time period. The behavior signal is provided for display via an interactive user interface and/or further processing.

18 Claims, 11 Drawing Sheets

(56) References Cited

U.S. PATENT DOCUMENTS

| | | | |
|---|---|---|---|
| 2015/0046181 A1 | 2/2015 | Adjaoute | |
| 2017/0193185 A1* | 7/2017 | Barker | G06F 16/334 |
| 2017/0270435 A1* | 9/2017 | Gallardo | G06N 3/0454 |
| 2018/0239870 A1* | 8/2018 | Goldman | G06Q 30/0185 |
| 2019/0205787 A1 | 7/2019 | Duriseti et al. | |

OTHER PUBLICATIONS

Che, Zhengping et al. "Distilling Knowledge From Deep Networks With Applications To Healthcare Domain," arXiv:1512.03542v1 [stat.ML] Dec. 11, 2015, pp. 1-13. [Retrieved From The Internet Apr. 7, 2020] <https://arxiv.org/pdf/1512.03542.pdf>.

Joudaki, Hossein et al. "Using Data Mining To Detect Health Care Fraud and Abuse: A Review Of Literature," Global Journal Of Health Science, vol. 7, No. 1, (2015), pp. 194-202. DOI: 10.5539/gjhs.v7n1p194. ISSN: 1916-9736. E-ISSN: 1916-9744.

Kreuzthaler, Markus et al. "EHR Problem List Clustering For Improved Topic-Space Navigation," BMC Medical Informatics and Decision Making, (2019), vol. 19 (Suppl 3):72, pp. 108-114. [Retrieved From The Internet Apr. 7, 2020] <https://bmcmedinformdecismak.biomedcentral.com/articles/10.1186/s12911-019-0789-9>.

Nestor. Bret et al. "Feature Robustness In Non-Stationary Health Records: Caveats To Deployable Model Performance In Common Clinical Machine Learning Tasks," arXiv:1908.00690v1 [cs.LG] Aug. 2, 2019, pp. 1-24. [Retrieved From The Internet Apr. 7, 2020] <https://arxiv.org/pdf/1908.00690.pdf>.

Ravi, Daniele et al. "Deep Learning For Health Informatics," IEEE Journal Of Biomedical and Health Informatics, vol. 21, No. 1, Jan. 2017, pp. 4-21. [Retrieved From The Internet Apr. 7, 2020] <https://ieeexplore.ieee.org/stamp/stamp.jsp?arnumber=7801947&tag=1>.

\* cited by examiner

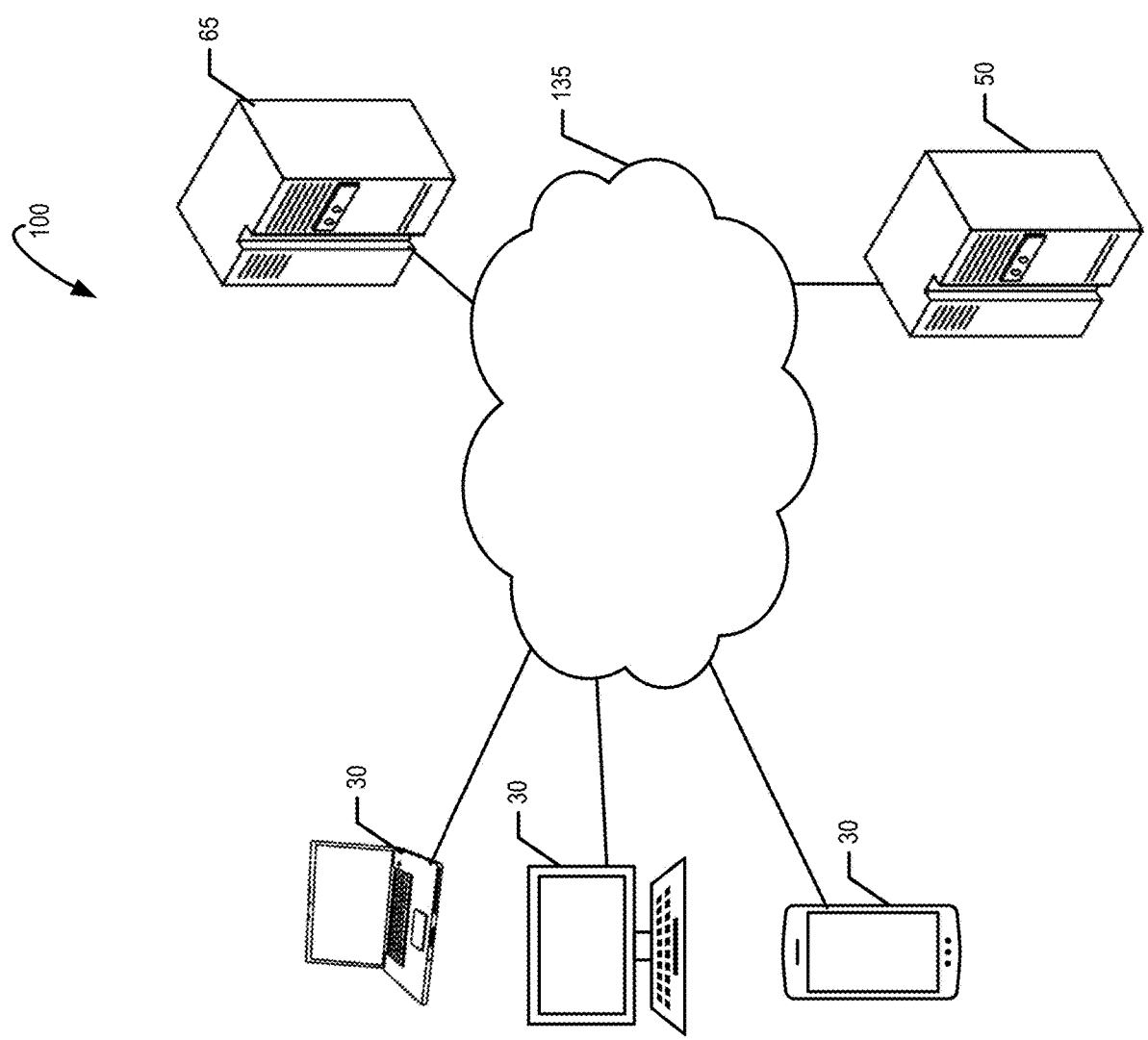

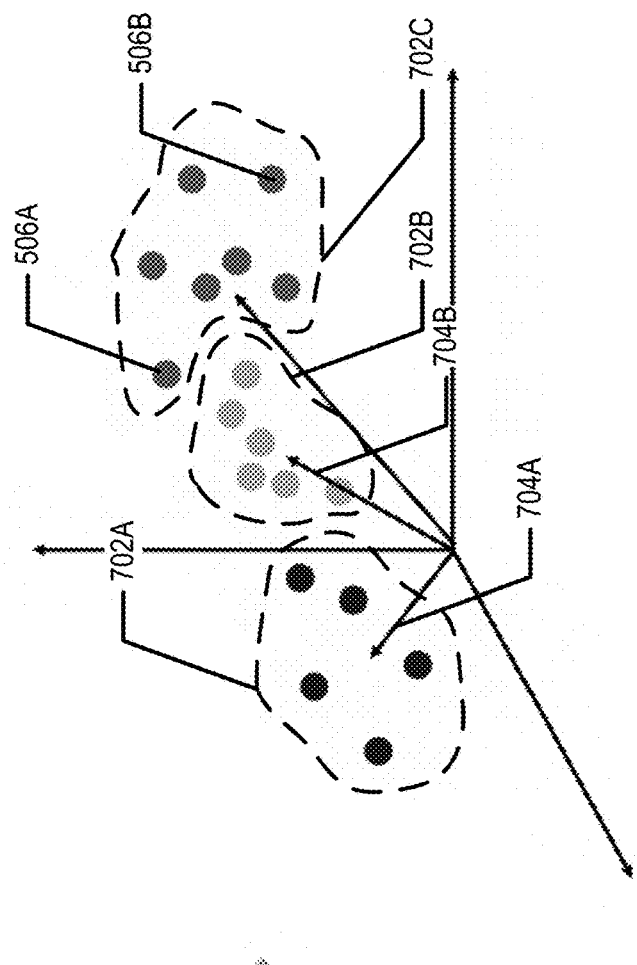
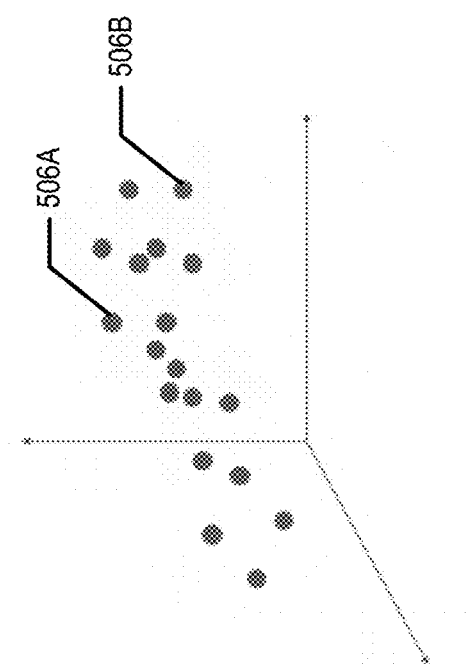
FIG. 7

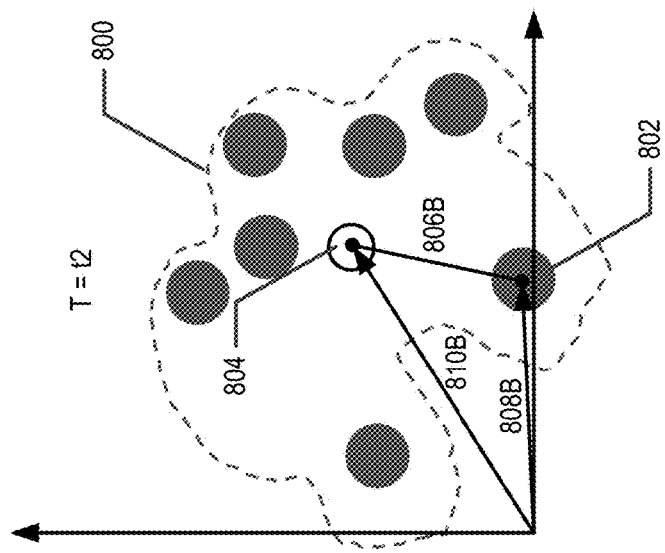
FIG. 8A
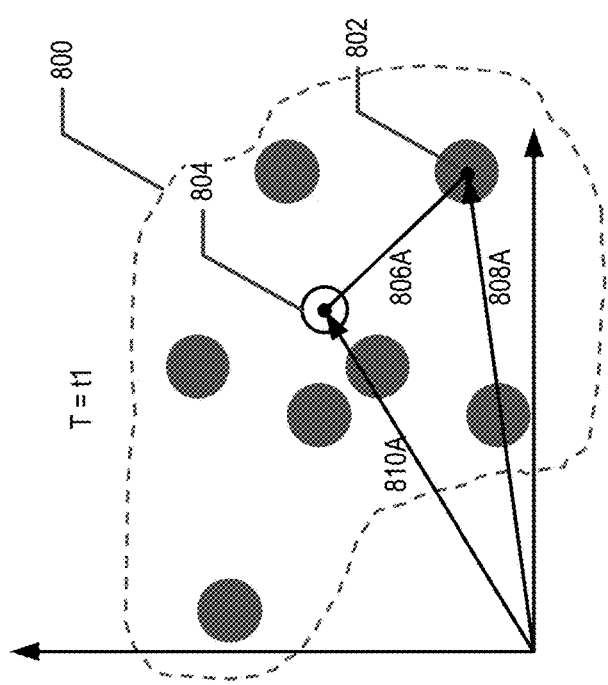
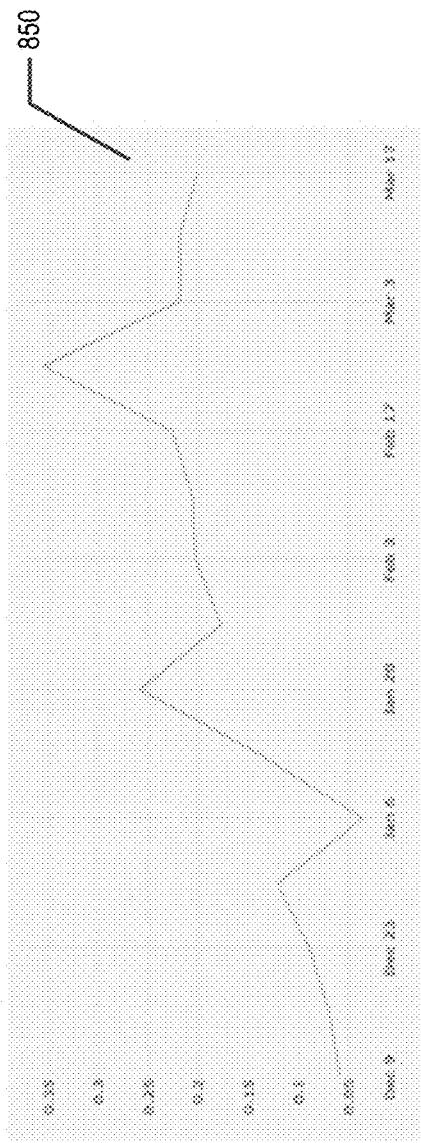
FIG. 8B

METHODS AND SYSTEMS FOR BEHAVIOR SIGNAL GENERATION AND PROCESSING

TECHNICAL FIELD

Various embodiments relate to the generation and processing of behavior signals. For instance, various embodiments generate behavior signals corresponding to medical provider behaviors.

BACKGROUND

In healthcare systems and their relevant components, members/patients and providers generate a high volume of claims for insurance companies. From the insurance company point of view, it is very important to track any abnormalities in the system and, more specifically, any abnormality in the submitted claims. Such abnormality tracking is important for detecting any gaming of the system that emerges from policies and claims. Currently various claim level abnormality detection are in place for medical cost saving purposes. However, detecting individual abnormal claims without providing insight to a larger picture is insufficient for detecting complex gaming behaviors of providers and members in the healthcare domain. Due to the infeasibility of having label data for these gaming behaviors, it is not possible to build supervised machine learning models to detect these patterns and trends from claim information/data.

BRIEF SUMMARY OF SOME EXAMPLE EMBODIMENTS

Various embodiments provide methods, systems, apparatus, computer program products, and/or the like for generating behavior signals for entities. In various embodiments, the entities are members/patients or providers (e.g., physicians, physician groups, and/or other healthcare providers). In various embodiments, the entities further include treatments, policies, states (e.g., government organizations and/or geographic regions), and/or the like. In various embodiments, the behavior signals indicate changes in entity cluster behavior, changes in entity behavior with respect to a peer cluster, changes in entity behavior with respect to the previous behavior of the entity, and/or the like. Various embodiments provide a fully automated end-to-end pipeline which is able to generate multiple behavior signals from raw claim information/data. For example, various embodiments generate one or more behavior signals without the use of manually labeled data. In various embodiments, the behavior signals are used to identify patterns in entity behavior, anomalous behavior, predict future entity behavior, and/or the like.

In various embodiments, instances of claim data/information are received and elements of claim features are extracted therefrom. Element vectors are generated for each extracted claim feature (e.g., via a vector embedding). For example, the categorical features of an instance of claim information/data may be embedded into an array of vectors using a machine-learning-trained Categorical to Vector model. The Categorical to Vector model may be a self-supervised model which learns the embeddings of elements of features of instances of claim information/data by considering the overall context of each claim in place of a training label. The numerical elements of the features of the instances of claim information/data may be normalized and/or scaled and combined with the array of vectors generated by Categorical to Vector model. This array may then be provided as input to an auto-encoder model (e.g., trained via a machine learning algorithm) to determine an anomaly score for each claim by calculating the re-construction error for the array of vectors (e.g., using the decoder portion of the auto-encoder) and to aggregate the array of vectors into a claim vector (e.g., using the encoder portion of the auto-encoder). For instance, the array of vectors determined based at least in part on the categorical and numerical elements of the features of the instances of claim information/data may be aggregated to generate a claim vector for the claim.

The claim vectors are grouped based at least in part on corresponding entities (e.g., a member/patient identified in the instance of claim information/data and/or a provider identified in the instance of claim information/data) and the group of claim vectors are aggregated to generate an entity vector. Entities may be clustered into entity clusters (e.g., member peer cluster, provider peer cluster, provider specialty cluster, and/or the like). Behavior signal values may be generated by comparing the entity vector corresponding to an entity with a cluster vector corresponding to an entity cluster with which the entity is affiliated and/or associated. In an example embodiment, a behavior signal value may be generated by comparing the entity vector corresponding to an entity to a previous entity vector corresponding to the entity.

In various embodiments, an entity profile corresponding to each entity is stored by an analysis computing entity. The entity profile corresponding to an entity may include an entity identifier (e.g., member identifier, provider identifier) configured to identify the entity, entity clusters with which the entity is affiliated and/or associated, behavior signals, and/or the like. For example, a behavior signal may comprise a plurality of behavior signal values that are time ordered. For example, each behavior signal value may be associated with a time. For instance, in an example embodiment, the instances of claim information/data for a day, week, month, quarter, and/or the like may be analyzed to generate a corresponding behavior signal value. The time-ordered sequence of a behavior signal values is a behavior signal that illustrates how an entities behavior has evolved over time with respect to an entity cluster that the entity is associated with, with respect the entity's own behavior, and/or the like. When a new behavior signal value is determined for the entity, the entity profile may be updated to include the new behavior signal value and to extend the corresponding behavior signal. The behavior signals for one or more entities may be provided for user review via an interactive user interface of a user computing entity, processed to identify patterns in the entity behavior and/or patterns in entity behavior corresponding to an entity cluster, used to predict future entity and/or entity cluster behavior, processed to generate entity suggestions, and/or the like.

According to one aspect, a method for tracking entity behavior over time. In an example embodiment, the method comprises receiving, by an analysis computing entity, one or more instances of claim data. Each instance of claim data corresponds to an entity and comprising one or more features. The method further comprises generating, by the analysis computing entity, a claim vector for each instance of claim data based at least in part on the one or more features of the instance of claim data; adding, by the analysis computing entity, the claim vector to a group of claim vectors, wherein each claim vector within the group of claim vectors corresponds to a same corresponding entity; and aggregating, by the analysis computing entity, each group of claim vectors to generate an entity vector corresponding to the corresponding entity. The method further comprises based at least in part on the entity vector and at least one of (a) an entity profile corresponding to the corresponding entity or (b) an entity cluster with which the corresponding entity is associated, determining, by the analysis computing entity, at least one behavior signal value for the corresponding entity; amending, by the analysis computing entity, a behavior signal to include the at least one behavior signal value, the behavior signal comprising at least two behavior signal values, each of the at least two behavior signal values associated with a time period; and providing, by the analysis computing entity, the behavior signal for at least one of (a) display via an interactive user interface of a user computing entity or (b) further processing for pattern identification and/or behavior prediction.

According to another aspect, an apparatus is provided. In an example embodiment, the apparatus comprises at least one processor, at least one communications interface, and at least one memory including computer program code. The computer program code comprises executable instructions. The at least one memory and computer program code are configured to, with the processor, cause the apparatus to at least receive one or more instances of claim data, each instance of claim data corresponding to an entity and comprising one or more features; generate a claim vector for each instance of claim data based at least in part on the one or more features of the instance of claim data; add the claim vector to a group of claim vectors, wherein each claim vector within the group of claim vectors corresponds to a same corresponding entity; aggregate each group of claim vectors to generate an entity vector corresponding to the corresponding entity; based at least in part on the entity vector and at least one of (a) an entity profile corresponding to the corresponding entity or (b) an entity cluster with which the corresponding entity is associated, determine at least one behavior signal value for the corresponding entity; amend a behavior signal to include the at least one behavior signal value, the behavior signal comprising at least two behavior signal values, each of the at least two behavior signal values associated with a time period; and provide the behavior signal for at least one of (a) display via an interactive user interface of a user computing entity or (b) further processing for pattern identification and/or behavior prediction.

According to yet another aspect, a computer program product is provided. In an example embodiment, the computer program product comprises at least one non-transitory computer-readable storage medium having computer-executable program code portions stored therein. The computer-executable program code portions comprise program code instructions. The computer program code instructions, when executed by a processor of a computing entity, are configured to cause the computing entity to receive one or more instances of claim data, each instance of claim data corresponding to an entity and comprising one or more features; generate a claim vector for each instance of claim data based at least in part on the one or more features of the instance of claim data; add the claim vector to a group of claim vectors, wherein each claim vector within the group of claim vectors corresponds to a same corresponding entity; aggregate each group of claim vectors to generate an entity vector corresponding to the corresponding entity; based at least in part on the entity vector and at least one of (a) an entity profile corresponding to the corresponding entity or (b) an entity cluster with which the corresponding entity is associated, determine at least one behavior signal value for the corresponding entity; amend a behavior signal to include the at least one behavior signal value, the behavior signal comprising at least two behavior signal values, each of the at least two behavior signal values associated with a time period; and provide the behavior signal for at least one of (a) display via an interactive user interface of a user computing entity or (b) further processing for pattern identification and/or behavior prediction.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 1 is a diagram of a system that can be used in conjunction with various embodiments of the present invention;

Figure 4:
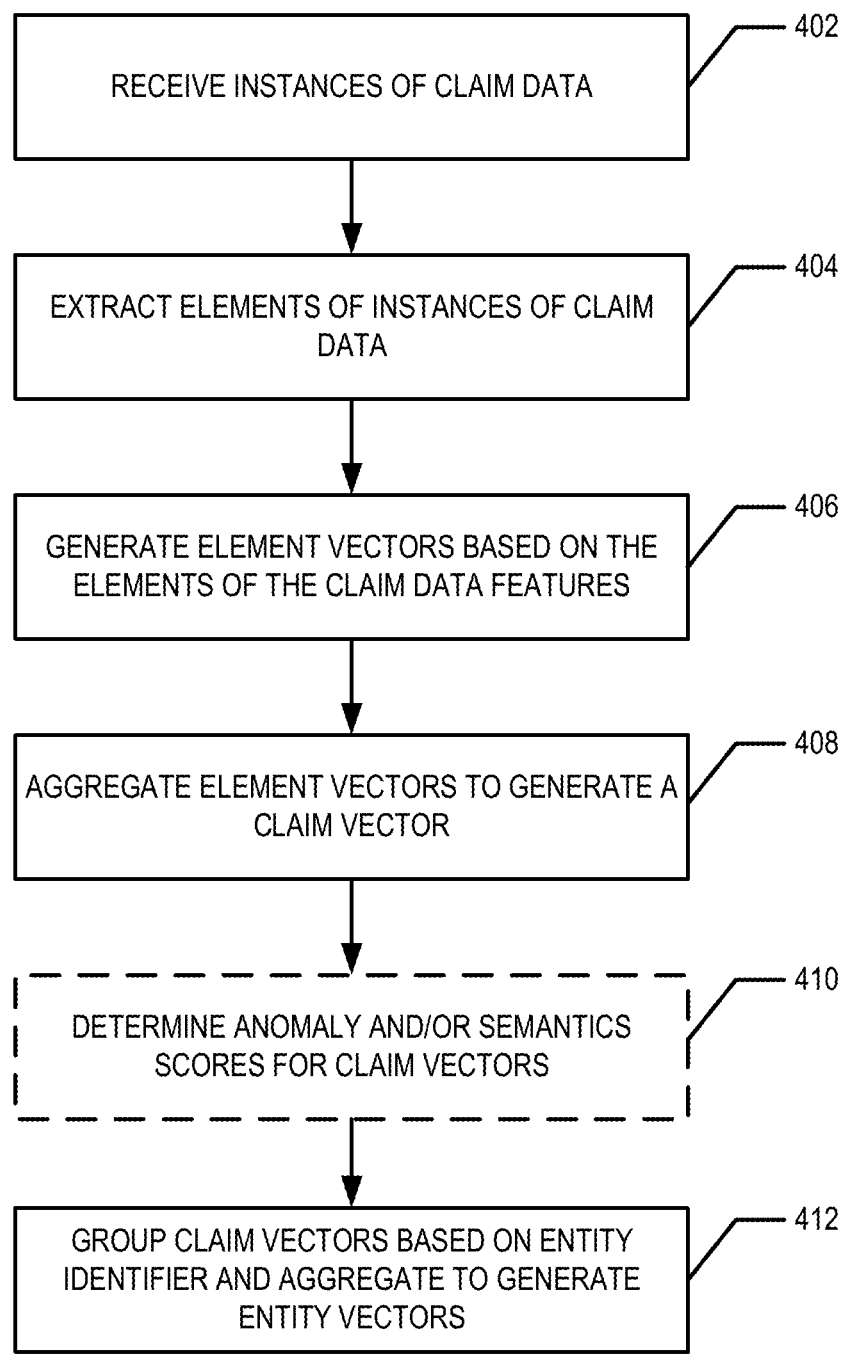
Figure 5B:
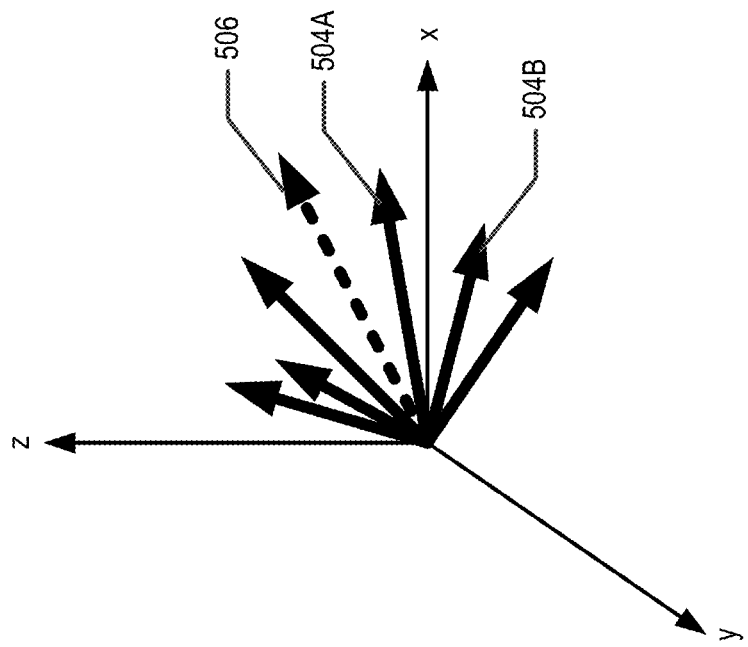
Figure 5A:
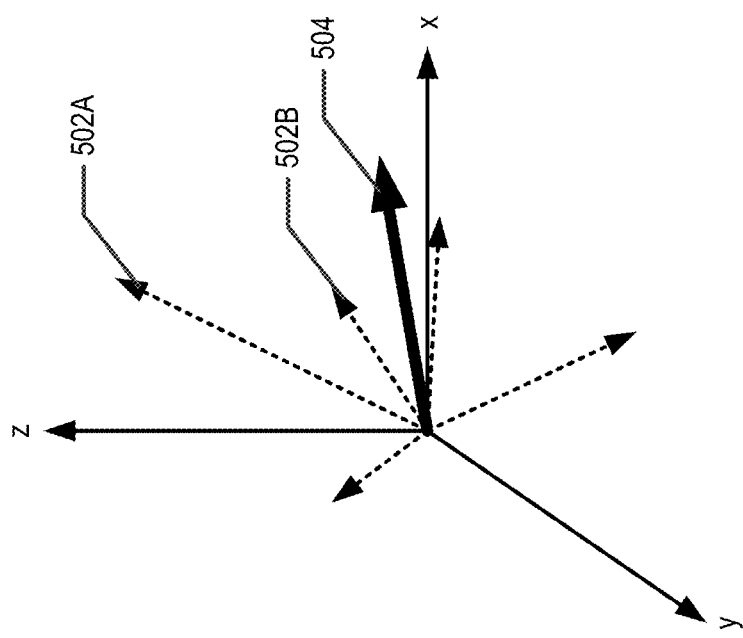
Figure 6:
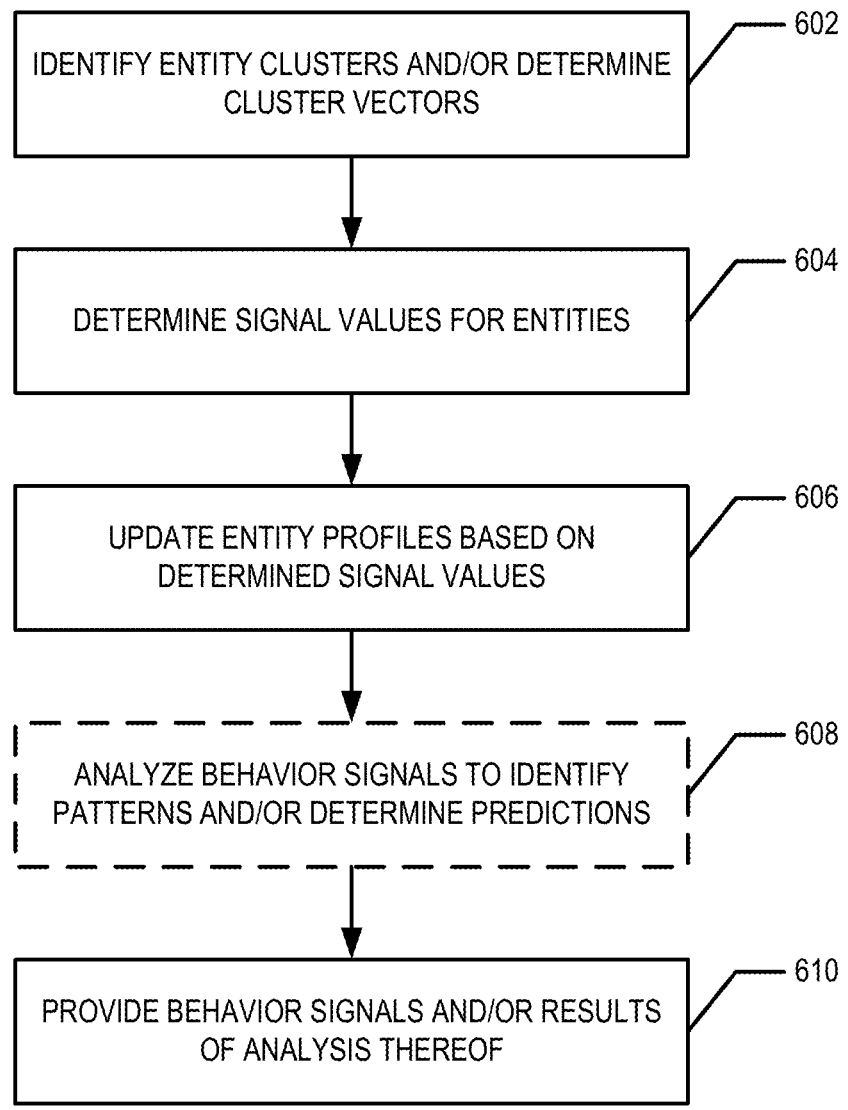
Figure 9:
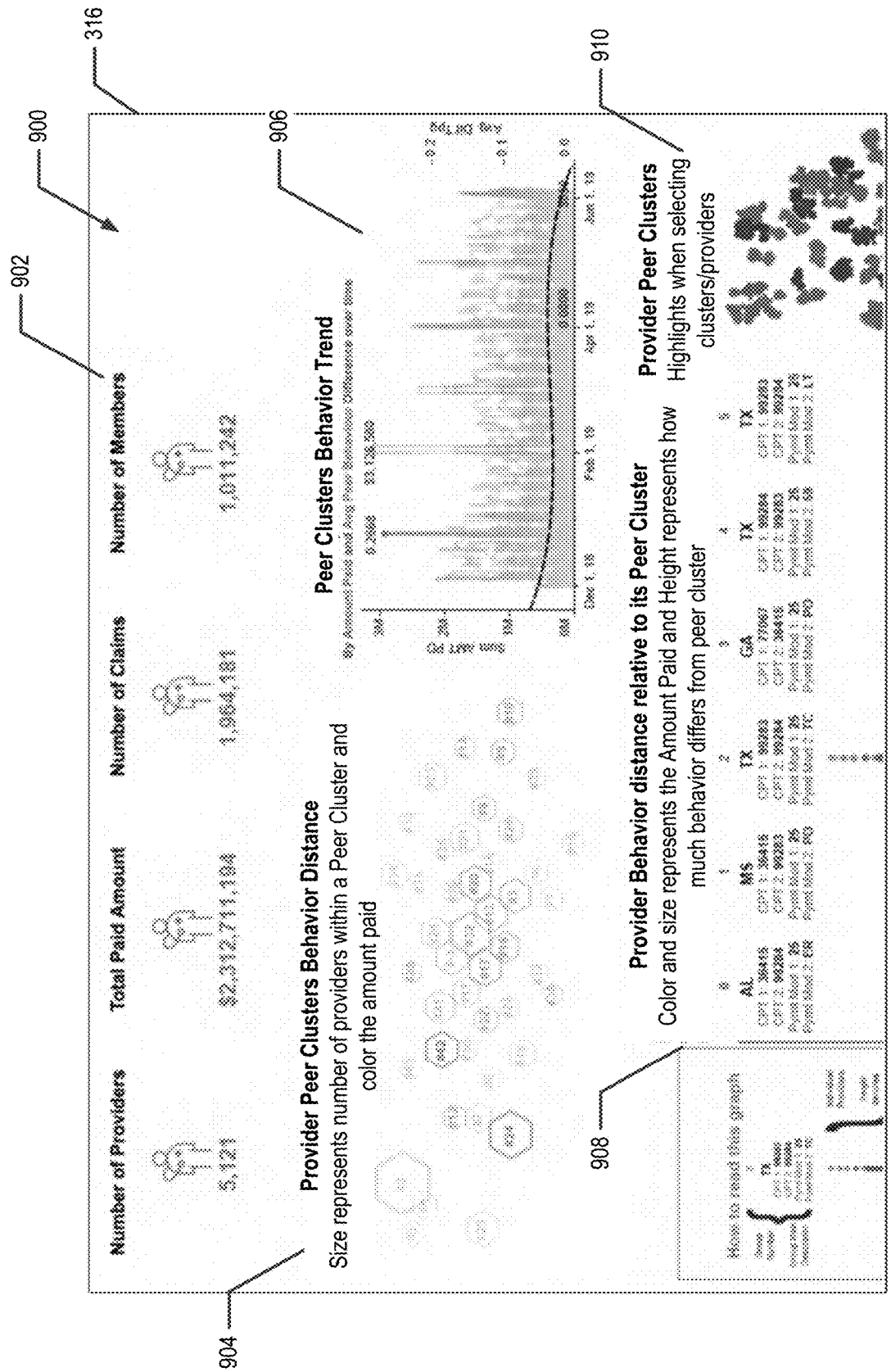
Figure 10:
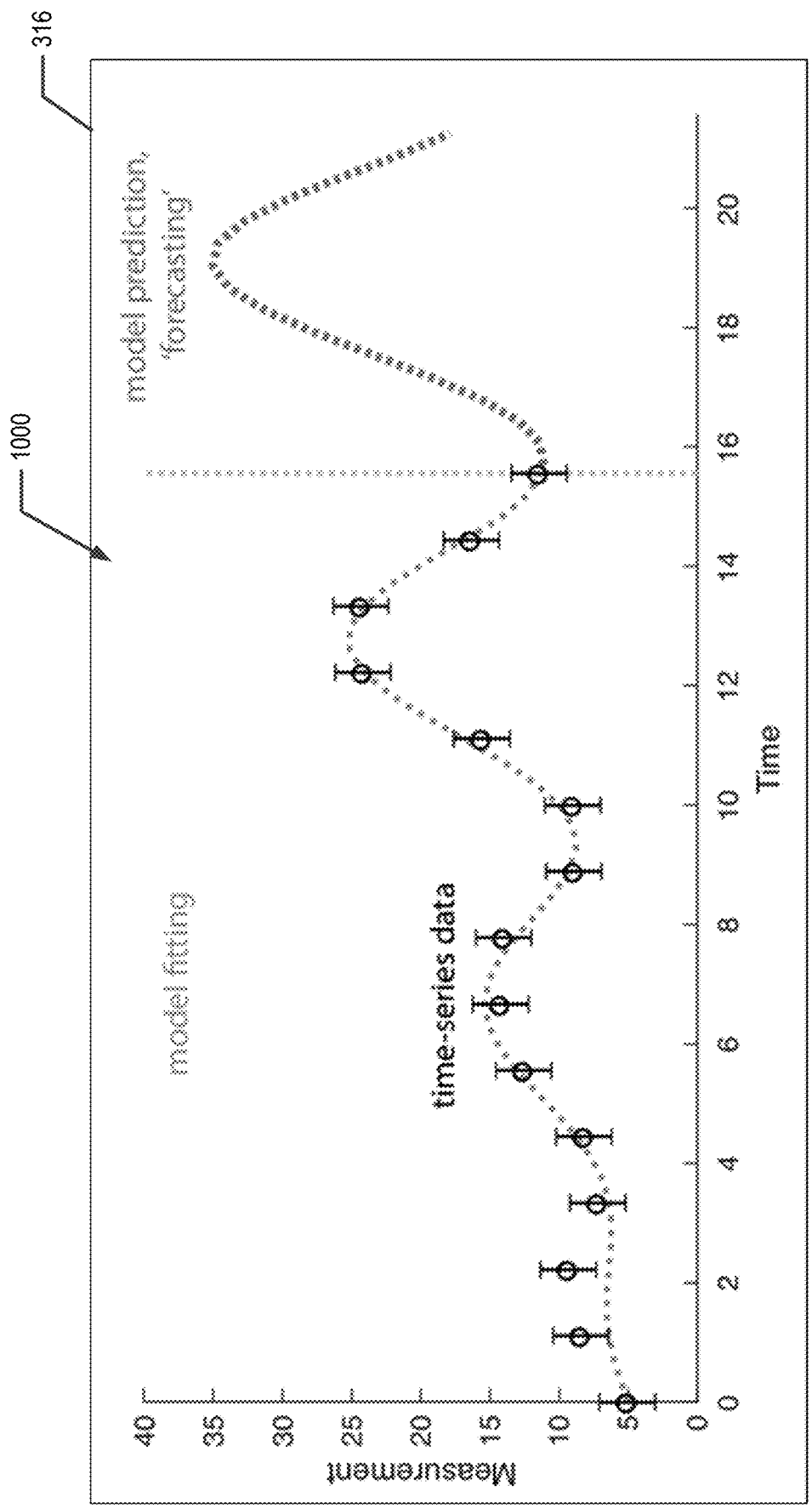

FIG. 4 provides a flowchart illustrating various processes, procedures, and/or operations performed to generate an entity vector from claim information/data, in accordance with certain embodiments of the present invention;

FIG. 5A illustrates an example of aggregating claim feature vectors to generate a claim vector, in accordance with certain embodiments of the present invention;

FIG. 5B illustrates an example of aggregating claim vectors to generate an entity vector, in accordance with certain embodiments of the present invention;

FIG. 6 provides a flowchart illustrating various processes, procedures, and/or operations performed to generate a behavior signal value and/or analyze a behavior signal, in accordance with certain embodiments of the present invention;

FIG. 7 is a schematic diagram illustrating the generation of entity clusters from entity vectors, in accordance with certain embodiments of the present invention;

FIG. 8A is a schematic diagram showing the evolution of behavior of an entity cluster and a particular entity with respect to the entity cluster over time, in accordance with certain embodiments of the present invention;

FIG. 8B illustrates a behavior signal, in accordance with certain embodiments of the present invention;

FIG. 9 illustrates an example dashboard provided as an interactive user interface via a user interface of a user computing entity, in an example embodiment; and FIG. 10 illustrates an example prediction dashboard view provided via the interactive user interface, in an example embodiment.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For instance, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of a system 100 that can be used in conjunction with various embodiments of the present invention. As shown in FIG. 1, the system 100 may comprise one or more analysis computing entities 65, one or more claim computing entities 50, one or more user computing entities 30, one or more networks 135, and/or the like. In various embodiments, the one or more user computing entities 30 comprise provider computing entities, patient/member computing entities, and/or insurance company affiliate computing entities (e.g., computing entities operated by employees of an insurance company). Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, stand-alone entities, the various embodiments are not limited to this particular architecture.

a. Exemplary Analysis Computing Entity

Figure 2A:
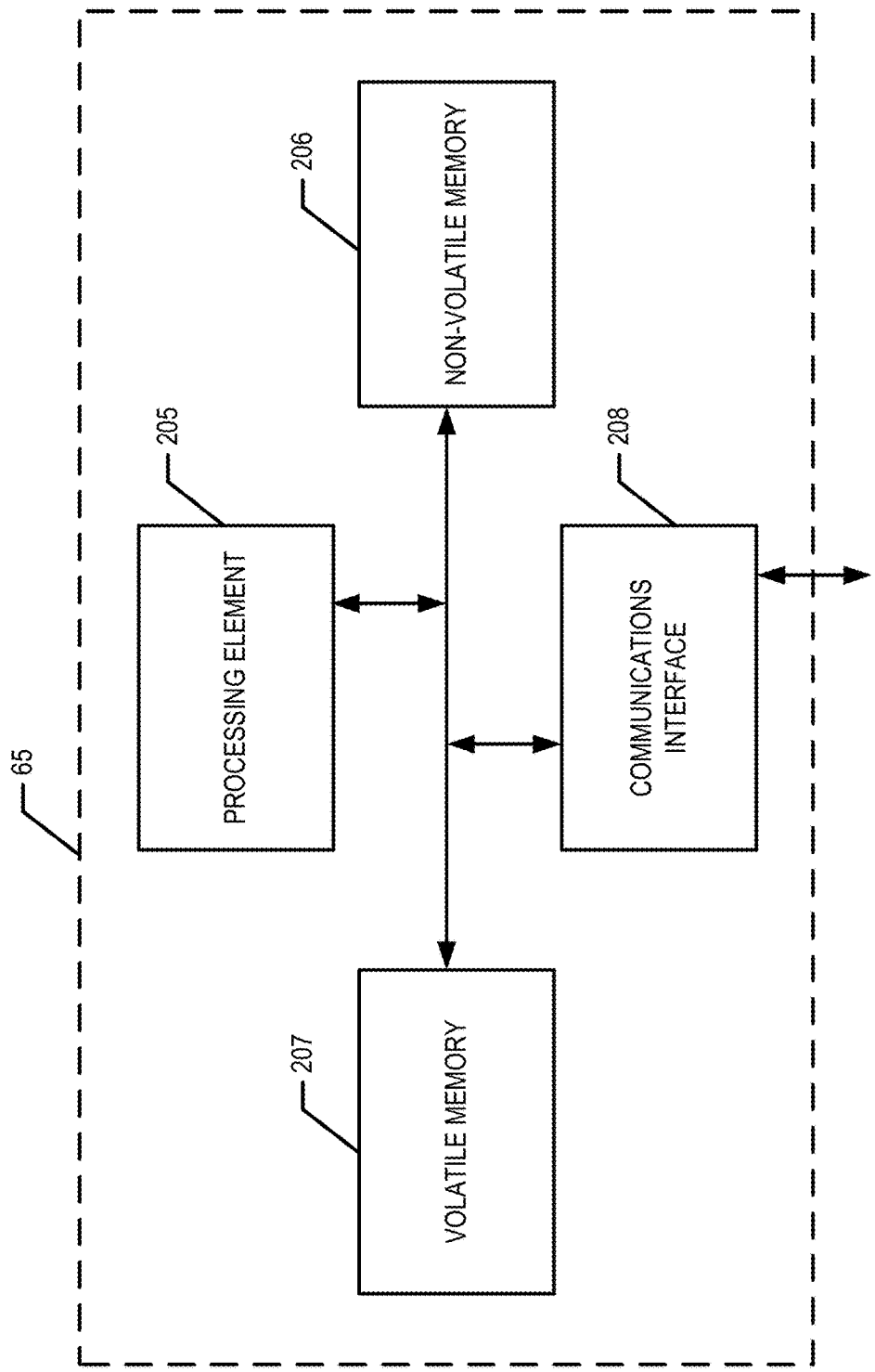
FIG. 2A is a schematic of an analysis computing entity in accordance with certain embodiments of the present invention.

FIG. 2A provides a schematic of an analysis computing entity 65 according to one embodiment of the present invention. In various embodiments, the analysis computing entity 65 executes one or more program modules, application program code, sets of computer executable instructions, and/or the like to generate behavior signal values for one or more entities, process behavior signals for one or more entities, and/or the like. In general, the terms computing entity, entity, device, system, and/or similar words used herein interchangeably may refer to, for instance, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the analysis computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analysis computing entity 65 may communicate with other computing entities, one or more user computing entities 30, and/or the like.

As shown in FIG. 2A, in one embodiment, the analysis computing entity 65 may include or be in communication with one or more processing elements 205 (also referred to as processors, processing circuitry, and/or similar terms used herein interchangeably) that communicate with other elements within the analysis computing entity 65 via a bus, for instance, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

Figure 2B:
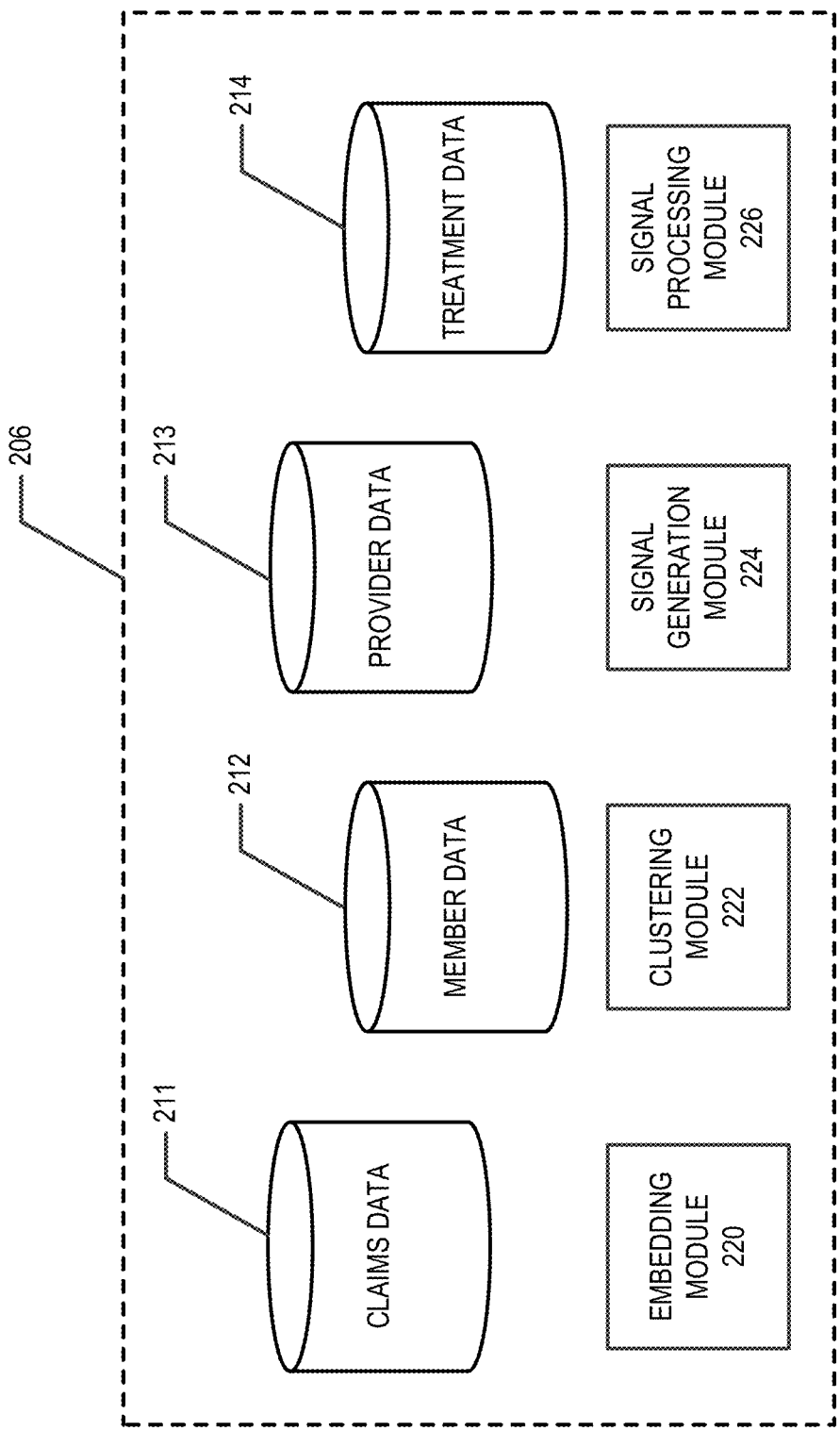
FIG. 2B is a schematic representation of a memory media storing a plurality of data assets.

In one embodiment, the analysis computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. For instance, as shown in FIG. 2B, the memory media 206 may store computer executable code that, when executed by the processing element 205, causes the operation of an embedding module 220, clustering module 222, signal generation module 224, signal processing module 226, and/or the like, which are described in detail elsewhere herein. Though described as modules herein, the embedding module 220, clustering module 222, signal generation module 224, and/or signal processing module 226 may be embodied by various forms of computer-executable instructions, program/application code, and/or the like, in various embodiments. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, metadata for data assets may be stored in metadata repositories encompassed within the memory media 206. The metadata for the data assets in the metadata data stores, metadata repositories, and similar words used herein interchangeably may comprise claims information/data 211, entity profiles (e.g., member information/data 212, provider information/data 213, and/or the like), treatment information/data 214, and/or various other types of information/data. In an example embodiment, the memory media 206 may store patient/member data repositories, provider data repositories, care standard data repositories, and/or the like. As will be recognized, metadata repositories are inventories data assets in an organization's environment.

In one embodiment, the analysis computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for instance, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the analysis computing entity 65 with the assistance of the processing element 205 and operating system.

As indicated, in one embodiment, the analysis computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analysis computing entity 65 may communicate with computing entities or communication interfaces of other computing entities 65, user computing entities 30, and/or the like. In this regard, the analysis computing entity 65 may access various data assets.

As indicated, in one embodiment, the analysis computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analysis computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analysis computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the central computing entity's components may be located remotely from other analysis computing entity 65 components, such as in a distributed system. Furthermore, one or more of the components may be aggregated and additional components performing functions described herein may be included in the analysis computing entity 65. Thus, the analysis computing entity 65 can be adapted to accommodate a variety of needs and circumstances.

b. Exemplary User Computing Entity

Figure 3:
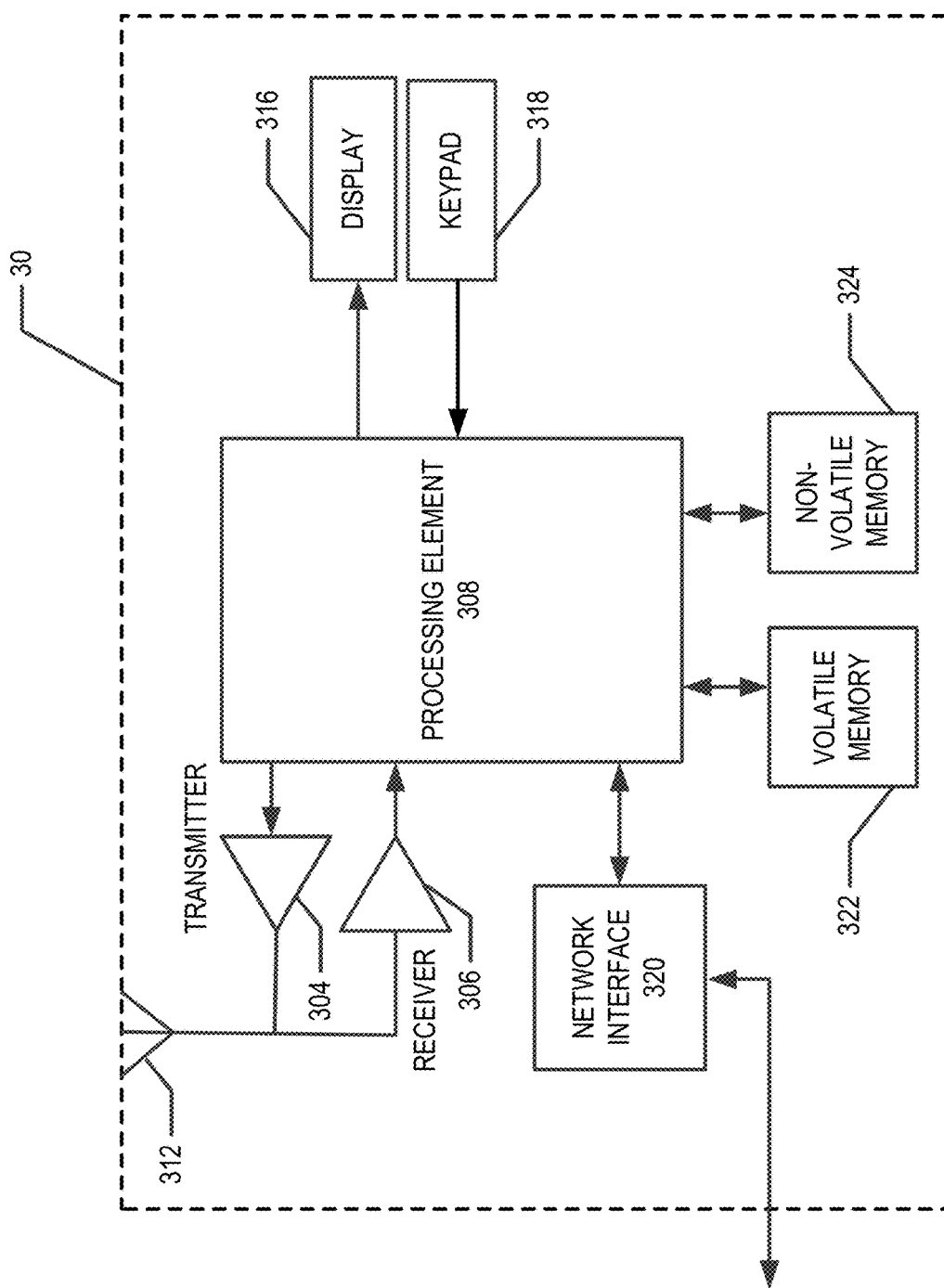
FIG. 3 is a schematic of a user computing entity in accordance with certain embodiments of the present invention.

FIG. 3 provides an illustrative schematic representative of user computing entity 30 that can be used in conjunction with embodiments of the present invention. In various embodiments, a user computing entity 30 may be a provider computing entity operated by and/or on behalf of a provider. In various embodiments, a provider is a healthcare provider; clinic; hospital; healthcare provider group; administrative and/or clinical staff associated with a healthcare provider, clinic, hospital, healthcare provider group, and/or the like; and/or other provider of healthcare services. In various embodiments, a user computing entity 30 is a patient/member computing entity. In various embodiments, a patient/member computing entity is operated by and/or on behalf of a patient and/or member of a policy, plan, and/or the like provided by an insurance company, payor, and/or other entity. In various embodiments, a user computing entity 30 is an insurance company affiliate computing entity. In various embodiments, an insurance company affiliate is an employee of an insurance company.

As will be recognized, the user computing entity may be operated by an agent and include components and features similar to those described in conjunction with the analysis computing entity 65. Further, as shown in FIG. 3, the user computing entity may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an analysis computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For instance, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for instance, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output devices/interfaces (e.g., a display 316 and/or speaker/speaker driver coupled to a processing element 308 and a touch screen, keyboard, mouse, and/or microphone coupled to a processing element 308). For example, the user output device/interface may be configured to provide an application, browser, interactive user interface (IUI), dashboard, webpage, Internet accessible/online portal, and/or similar words used herein interchangeably executing on and/or accessible via the user computing entity 30 to cause display or audible presentation of information/data and for user interaction therewith via one or more user input devices/interfaces. The user output interface may be updated dynamically from communication with the analysis computing entity 65. The user input device/interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input device/interface can be used, for instance, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Claims Computing Entity

In various embodiments, a claims computing entity 50 is a computing entity configured to receive, process, and/or provide claims information/data. In various embodiments, a claims computing entity 50 may receive instances of claims information/data provided, for instance, by a user computing entity 30. The claims computing entity 50 may process the instances of claims information/data (e.g., to process the corresponding claims) and/or may provide (e.g., transmit) instances of claims information/data such that an analysis computing entity 65 receives the instances of claims information/data. In various embodiments, a claims computing entity 50 comprises one or more components similar to those described above with respect to the analysis computing entity 65 and/or the user computing entity 30. For example, the claims computing entity 50 may comprise one or more processing elements, memories (e.g., volatile and/or non-volatile), communication interfaces, user interfaces, and/or the like.

d. Exemplary Networks

In one embodiment, the networks 135 may include, but are not limited to, any one or a combination of different types of suitable communications networks such as, for instance, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. TECHNICAL ADVANTAGES

Various embodiments provide an automated technique for identifying anomalous entity behavior, predicting future entity behavior, identifying and monitoring entity behavior patterns, generating suggestions for improvement of entity behavior, and/or the like. For instance, in the healthcare domain, insurance providers process millions of claims. However, traditional techniques for identifying anomalous claims fail to identify patterns of entity behavior that are anomalous. Embodiments of the present invention provide a technical solution to this problem by not only identify anomalous patterns of entity behavior, but also providing predictions of entity behavior, suggestions for improvement of entity behavior and/or the like in an automated manner. The high volume of claims to be processed requires that such a solution be a technical computer-based solution. Thus, various embodiments provide technical solutions to technical problems related to identifying patterns of entity behavior based at least in part on, for example, claim information/data and enabling improvement of entity behavior and the healthcare environment based at least in part on the identified patterns.

IV. EXEMPLARY SYSTEM OPERATION

As described above, various embodiments are configured to transform and analyze claim information/data to identify patterns in entity behavior. These identified patterns in entity behavior may be used to monitor entity behavior, identify anomalous patterns of entity behavior, determine suggestions for improvement of entity behavior, determine predictions of future entity behavior based at least in part on various external factors, and/or the like in an automated fashion. For instance, various embodiments provide an automated technique for receiving, transforming, and analyzing claim information/data to provide monitoring of entity behavior, identification of anomalous patterns of entity behavior, determination of suggestions for improvement of entity behavior, determination of predictions of future entity behavior based at least in part on various external factors, and/or the like.

In various embodiments, a claims computing entity 50 receives claims from various user computing entities 30 (e.g., provider computing entities, user computing entities, and/or the like). Each claim provides an instance of claim information/data. Each instance of claim information/data comprises a plurality of features such as entity identifying information/data, categorical elements, numerical elements, temporal information/data, and/or the like. For example, each instance of claim information/data comprises entity identifying information/data such as a member/patient identifier configured to identify the member/patient corresponding to the claim, a provider identifier configured to identify the provider corresponding to the claim, a location corresponding to the claim (e.g., a location where the service(s) and/or product(s) identified in the claim were provided to the patient/member), member demographic information/data (e.g., gender, age/age group, etc.), and/or the like. In various embodiments each instance of claim information/data comprises categorical elements. In various embodiments, the categorical elements comprise medical codes (e.g., current procedural terminology (CPT) codes and/or the like) such as one or more diagnosis codes, procedure codes, medication codes, equipment codes, and/or other medical codes that describe the service(s) and/or product(s) provided to the member/patient in one or more transactions corresponding to the claim. In various embodiments, a vector embedding may be used to transform one or more categorical elements of the claims into vectors in a multi-dimensional space. For instance, as described in U.S. application Ser. No. 15/927,188, filed Mar. 21, 2018, various medical codes may be transformed into vectors in a multi-dimensional space such that the distance between two vectors provides an indication of the similarity and/or relationship between the corresponding codes. In various embodiments, a machine-learning-based model is used to transform the categorical elements into element vectors. For example, a plurality of element vectors may be generated based at least in part on the categorical elements of an instance of claim information/data. In various embodiments, the numerical elements comprise numerical information/data corresponding to the member/patient and/or the service(s) and/or product(s) provided to the member/patient in one or more transactions corresponding to the claim. Some non-limiting examples of numerical elements include payment values, a member/ patient's age, number of units of a product provided, and/or the like. In various embodiments, a numerical element may be associated with a categorical element. For instance, an associated categorical element may provide context for the numerical value of the numerical element. In various embodiments, the numerical elements of an instance of claim information/data may be normalized, rescaled, and/or the like (e.g., based at least in part on the associated categorical elements). In an example embodiment, the normalized, rescaled, and/or the like numerical elements and the associated categorical elements and/or corresponding element vectors may be provided to a machine-learning-based model. For example, the normalized, rescaled, and/or the like numerical elements and the associated categorical elements and/or corresponding element vectors may be provided to an auto-encoder network. The machine-learning-based model may be configured to determine, calculate, and/or the like a claim vector by aggregating the element vectors (e.g., based at least in part on the associated numerical elements and/or normalized, rescaled, and/or the like numerical elements), an anomaly score for the claim vector, and/or the like. In various embodiments, each instance of claim information/data comprises temporal information/data corresponding to the date and/or time at which the service(s) and/or product(s) corresponding to the claim were provided to the patient/member.

In various embodiments, a plurality of claim vectors are determined based at least in part on a plurality of instances of claim information/data. Each claim vector is associated with a provider identifier and a member/patient identifier. The claim vector is associated with the corresponding provider and/or member/patient. For instance, an entity profile corresponding to the provider (e.g., stored in provider data 213) identified by the provider identifier of the claim and/or the patient/member (e.g., stored in member data 212) identified by the member/patient identifier of the claim may be amended to include the claim vector and/or corresponding metadata (e.g., patient/member identifier, provider identifier, temporal information/data, and/or the like). In various embodiments, the claim vectors associated with an entity and a time period are aggregated to generate an entity vector corresponding to the time period. For example, an entity vector may be generated daily, weekly, biweekly, monthly, and/or the like. For instance, if an entity vector corresponds to a time period of the month of January 2020, all of the claim vectors having temporal information/data corresponding to a time in January 2020 (e.g., services and/or products were provided by the provider to the member/patient in January 2020) may be aggregated to generate an entity vector corresponding to January 2020.

In various embodiments, the element vectors are determined in a multi-dimensional space. In various embodiments, this may be a very high dimensional space (e.g., hundreds of dimensions). In various embodiments, the claim vectors and/or entity vectors may be transformed and/or mapped into a lower multi-dimensional space. For example, the entity vectors may be defined in a high dimensional embedding space and the dimensionality of the embedding space may be reduced using a Uniform Manifold Approximation and Projection (UMAP) algorithm, and/or the like. In various embodiments, the dimension reduction process is configured to maintain one or more relationships (e.g., distances) between various claim and/or entity vectors.

In various embodiments, the entity vectors corresponding to providers may be analyzed to identify one or more provider clusters. In various embodiments, provider clusters may be geographic clusters identified based at least in part on the geographic location in which providers practice (e.g., providers practicing the southeast, providers practicing in the state of Texas, provider practicing in the Chicago metro-area, and/or the like). In various embodiments, provider clusters are specialty clusters identified based at least in part on provider specialties (e.g., gastroenterologists, urologists, gynecologists, and/or the like). In various embodiments, provider peer clusters may be identified based at least in part on provider behavior as indicated by the entity vectors associated with the providers. For instance, a density-based clustering method may be used to identify one or more provider peer clusters based at least in part on the entity vectors corresponding to the providers in the (reduced) multi-dimensional space. For example, a hierarchical density-based spatial clustering of applications with noise (HDBSCAN) clustering algorithm and/or another clustering algorithm may be used to identify provider peer clusters (and/or member peer clusters). Similarly, member/patient clusters may be identified using a geographic location associated with the member/patient (e.g., associated with the corresponding member profile stored in the member data 212), one or more diagnostic codes associated with the member/patient, and/or using a density-based (or other) clustering method based at least in part on the entity vectors corresponding to the members to identify member peer clusters. In various embodiments, treatment clusters may also be identified. In an example embodiment, the treatment clusters are determined and/or identified by a model trained only on the medical features of the claims information/data. For example, only the medical codes extracted from each instance of claim information/data may be used to generate multi-dimensional vectors which may the ben clustered for the sake of identifying treatment clusters. Treatment cluster identifiers may be assigned to the treatment clusters and these treatment cluster identifiers may then be used to primary model. In various embodiments, cluster identifiers configured to identify the clusters an entity is a member of are stored in the corresponding entity profile (e.g., in member data 212 and/or provider data 213).

In various embodiments, a cluster vector may be determined for one or more clusters. For instance, provider specialty cluster may comprise entity vectors for a plurality of a providers. The entity vectors for the plurality of providers may be aggregated to generate a cluster vector for the provider specialty cluster. Cluster vectors for various identified clusters may be similarly determined and/or generated by aggregating the entity vectors of the entities of the clusters.

In various embodiments, one or more signal values may be determined, calculated, and/or the like. An example signal value determined, calculated, and/or the like in an example embodiment is a provider behavior distance from peer cluster. In various embodiments, the provider behavior distance from peer cluster is the distance between an entity vector corresponding to the provider and the cluster vector of the peer cluster corresponding to and/or associated with the provider. Another example signal value determined, calculated, and/or the like in an example embodiment is a provider behavior distance from specialty cluster. In various embodiments, the provider behavior distance from specialty cluster is the distance between an entity vector corresponding to the provider and the cluster vector of the provider specialty cluster corresponding to and/or associated with the provider. Another example signal value determined, calculated, and/or the like in an example embodiment is a member-provider signal value corresponding to the member behavior distance from provider. In various embodiments, the member behavior distance from provider is the distance between an entity vector corresponding to the member and the entity vector corresponding to a provider associated with the member (e.g., a provider corresponding to a provider identifier of an instance of claim information/data that also includes the member identifier corresponding to the member/patient). Another example signal value determined, calculated, and/or the like in an example embodiment is a provider behavior distance from specialty cluster. In various embodiments, the provider behavior distance from specialty cluster is the distance between an entity vector corresponding to the provider and the cluster vector of the provider specialty cluster corresponding to and/or associated with the provider. In an example embodiment, another signal value that may be determined is the distance between an entity vector corresponding to a provider and a particular treatment (e.g., the vector embedding of a medical code corresponding to the treatment). Another example signal value determined, calculated, and/or the like in an example embodiment, is the distance between an entity vector corresponding to a provider and a member cluster vector.

In various embodiments, one or more signal values that correspond to changes in time may be determined. For example, a provider profile corresponding to a provider and stored in the provider data 213 may include entity vectors corresponding to the provider and corresponding to earlier/previous time periods. Similarly, a member profile corresponding to a member/patient and stored in the member data 212 may include entity vectors corresponding to the member and corresponding to earlier/previous time periods. In various embodiments, the one or more signal values comprise at least one signal value that is the distance between an entity or cluster vector corresponding to a first time period and an entity or cluster vector corresponding to a previous time period (e.g., immediately preceding time period and/or the like). For instance, a change of provider behavior with time signal value may be determined. In an example embodiment, the change of provider behavior with time signal value is the distance between (a) the entity vector corresponding to the provider and corresponding to the first time period and (b) the entity vector corresponding to the provider and corresponding to the previous time period (e.g., the immediately preceding time period). For example, a change in peer cluster behavior with time signal value may be determined. In an example embodiment, the change of peer cluster behavior with time signal value is the distance between (a) the cluster vector corresponding to the provider peer cluster and corresponding to the first time period and (b) the cluster vector corresponding to the provider peer cluster and corresponding to the previous time period (e.g., the immediately preceding time period). For instance, a change in specialty cluster behavior with time signal value may be determined. In an example embodiment, the change of specialty cluster behavior with time signal value is the distance between (a) the cluster vector corresponding to the provider specialty cluster and corresponding to the first time period and (b) the cluster vector corresponding to the provider specialty cluster and corresponding to the previous time period (e.g., the immediately preceding time period). For example, a change of member behavior with time signal value may be determined. In an example embodiment, the change of member behavior with time signal value is the distance between (a) the entity vector corresponding to the member/patient and corresponding to the first time period and (b) the entity vector corresponding to the member/patient and corresponding to the previous time period (e.g., the immediately preceding time period).

In various embodiments, a variety of distance measurements may be used to determine, generate, and/or calculate the signal values, such as Euclidean distance, cosine distance, and/or other distance measurement.

These signal values and corresponding metadata (e.g., provider identifier, member identifier, time period, cluster identifier configured to identify the corresponding peer cluster or specialty cluster, and/or the like as appropriate for the signal value) may be stored (e.g., in the corresponding member and/or provider profiles and/or in a separate behavior signal data store). A behavior signal comprises a time ordered series of corresponding signal values. For instance, the provider behavior signal comprises a provider behavior signal value corresponding to a time t1, a provider behavior signal value corresponding to a time t2, and/or the like with each of the provider behavior signal values ordered in chronological order of the corresponding times.

The behavior signals may be analyzed to determine patterns in provider behavior for an individual provider, patterns in behavior of clusters of providers (e.g., peer clusters, specialty clusters, and/or the like), pattern in behavior of particular members, and/or the like. In various embodiments, these behavior signals may be monitored to identify changes in entity and/or entity cluster behaviors. In various embodiments, the behavior signals and patterns identified therefrom may be used to identify entities exhibiting anomalous behavior (e.g., providers and/or members/patients exhibiting anomalous behavior), in various embodiments. In various embodiments, the behavior patterns may be used to determine suggestions for changes in behavior that may improve an entity's behavior. For example, a first provider may routinely submit claims including a particular medical code and other providers within a peer cluster or specialty cluster that comprises the first provider may routinely submit claims including a different, but similar medical code. Thus, the first provider's behavior may appear anomalous due to this different but similar medical code usage. A suggestion may then be determined, generated, and/or the like (and provided to the first provider) that the first provider should use the different but similar medical code rather than the particular medical code, as appropriate. In another example, the behavior signals may be used to generate predictions of entity and/or entity cluster behaviors responsive to various external factors (e.g., insurance company and/or government policy changes, provider ratings, pricing changes, insurance plan changes, news, events, and/or other happenings that are not governed and/or controlled by a particular entity (e.g., provider or member/patient)).

FIG. 4 provides a flowchart illustrating various processes, procedures, operations, and/or the like that may be performed (e.g., by an analysis computing entity 65) to generate an entity vector corresponding to an entity (e.g., member/patient or provider) and corresponding to a time period, according to an example embodiment. Starting at step/operation 402, instances of claims information/data are received. For instance, user computing entities 30 (e.g., provider computing entities and/or member computing entities) may be submit claims that are received by a claims computing entity 50. The claims computing entity 50 may provide instances of claim information/data corresponding to the claims such that the analysis computing entity 65 receives the instances of claim information/data. For example, the analysis computing entity 65 may comprise means, such as processing element 205, memory (e.g., volatile memory 207 and/or non-volatile memory 206), communications interface 208, and/or the like, configured for receiving instances of claim information/data. As noted above, an instance of claim information/data may comprise a plurality of elements such as entity identifying information/data, categorical elements, numerical elements, temporal information/data, and/or the like. In various embodiments, the instances of claim information/data correspond to a time period. For instance, the temporal information/data of the instances of claim information/data indicate that the service(s) and/or product(s) corresponding to the instance of claim information/data was performed and/or provided during the time period. In an example embodiment, the time period may correspond to a day, a week, a two week period, a month, a quarter (e.g., a three month period), a year, and/or the like.

At step/operation 404, the elements of the instances of claim information/data are extracted. For example, the analysis computing entity 65 may extract elements of the instances of claim information/data. For instance, the analysis computing entity 65 may comprise means, such as processing element 205, memory (e.g., volatile memory 207 and/or non-volatile memory 206), and/or the like for extracting elements of the instances of claim information/data. For example, categorical and/or numerical elements of the instances of claim information/data may be extracted from the instances of claim information/data. In an example embodiment, each extracted element is associated with metadata that includes a claim identifier identifying the corresponding claim, a member identifier extracted from the corresponding claim, a provider identifier extracted from the corresponding claim, temporal information/data extracted from the corresponding claim, and/or the like. In an example embodiment, extracting the elements from an instance of claim information/data may include transforming an instance of claim information/data into a particular format comprising an array of categorical elements and any corresponding numerical elements.

At step/operation 406, the extracted elements of the instances of claim information/data are transformed into element vectors. In an example embodiment, element vectors are generated based at least in part on the extracted elements of the instances of claim information/data. For instance, an embedding module 220 operating on the analysis computing entity 65 may determine, generate, and/or the like, an element vector for each of the extracted elements. For example, the analysis computing entity 65 may comprise means, such as processing element 205, memory (e.g., volatile memory 207 and/or non-volatile memory 206), and/or the like for determining, generating, and/or the like element vectors based at least in part on the extracted elements of the instances of claim information/data. In various embodiments, the metadata associated with an extracted element is associated with the corresponding element vector. For instance, the claim identifier, any entity identifier, any temporal information/data and/or the like associated with an extracted element may be associated with the corresponding element vector.

In various embodiments, the embedding module 220 is a machine-learning-based model. For example, the embedding module 220 may be a classifier and/or other model configured to generate vectors corresponding to categorical elements of instances of claim information/data such that the vectors encode relationships between the categorical elements. For instance, a first categorical element may be a medical code corresponding to a right arm break, a second categorical element may be a medical code corresponding to a left arm break, and a third categorical element may be a medical code corresponding to strep throat. The embedding module 220 may generate a first vector corresponding to the first categorical element, a second vector corresponding to the second categorical element, and a third vector corresponding to the third categorical element. The first vector and second vector may be close to one another (e.g., have a relatively small distance therebetween) and the third vector may be a larger distance from the first and second vectors, thus indicating that a right arm break and a left arm break are more similar to one another than either a right arm break or a left arm break is to strep throat. In an example embodiment, the embedding module 220 may use a library that was previously generated (e.g., based at least in part on training of a machine-learning-based model on instances of claim information/data and/or other medical information/data for a previous time period) to assign, generate, and/or determine element vectors for the extracted elements.

At step/operation 408, claim vectors may be generated. For example, the analysis computing entity 65 may generate claim vectors from the element vectors. For instance, the analysis computing entity 65 may comprise means, such as processing element 205, memory (e.g., volatile memory 207 and/or non-volatile memory 206), and/or the like for generating a claim vector from a plurality of element vectors. For example, the element vectors may be sorted by the associated metadata. For instance, all element vectors associated with a first claim identifier may be aggregated together to generate a first claim vector corresponding to the first claim identifier and all of the element vectors associated with a second claim identifier may be aggregated together to generate a second claim vector corresponding to the second claim identifier. For example, FIG. 5A illustrates an example plurality of element vectors 502 (e.g., 502A, 502B, shown as dashed lines). The plurality of element vectors 502 are aggregated to generate the corresponding claim vector 504 (shown as the thick solid line). In an example embodiment, aggregating the element vectors 502 to generate the corresponding claim vector 504 comprises performing a vector addition of the element vectors 502. In an example embodiment, aggregating the element vectors 502 to generate the corresponding claim vector 504 comprises performing an average of the element vectors 502. In an example embodiment, the element vectors 502 are aggregated by the embedding module 220 and/or a portion thereof (e.g., a machine learning trained auto-encoder network and/or the like) to generate the corresponding claim vector 504. In various embodiments, a variety of methods may be used to aggregate the element vectors 502 associated with a common claim identifier to generate a claim vector associated with the claim identifier.

Continuing with FIG. 4, at optional step/operation 410, an anomaly score (e.g., reconstruction error), infused semantics score, and/or the like for an instance of claim information/data are determined. For instance, one or more element vectors corresponding to a claim vector and/or the claim vector may be provided to a trained auto-encoder network. The auto-encoder network may determine an anomaly score (e.g., reconstruction error), infused semantics score, and/or the like based at least in part on the one or more element vectors and/or claim vector. In an example embodiment, the auto-encoder network may be part of the embedding module 220. For example, the analysis computing entity 65 may comprise means, such as processing element 205, memory (e.g., volatile memory 207 and/or non-volatile memory 206), and/or the like, for determining an anomaly score, infused semantics score, and/or the like for an instance of claim information/data.

At step/operation 412, the claim vectors are grouped based at least in part on entity identifiers associated therewith and aggregated to generate entity vectors. For instance, a claim vector may be associated with metadata that includes a claim identifier, member identifier, provider identifier, and/or the like. The claim vectors corresponding to the time period may be grouped such that all of the claim vectors associated with a first provider identifier are aggregated to generate an entity vector corresponding to the first provider (e.g., identified by the first provider identifier) and corresponding to the time period. In various embodiments, the claim vectors may be grouped by member identifier to generate entity vectors each corresponding to a member. In various embodiments, the claim vectors may be grouped by provider identifier to generate entity vectors each corresponding to a provider. For example, claim vectors associated with a common provider identifier may be aggregated to generate an entity vector corresponding to the provider identified by the common provider identifier. For instance, FIG. 5B illustrates an example plurality of claim vectors 504 (e.g., 504A, 504B, shown as thick solid lines). The plurality of claim vectors 504 are aggregated to generate the corresponding entity vector 506 (shown as the thick dotted line). In an example embodiment, aggregating the claim vectors 504 to generate the corresponding entity vector 506 comprises performing a vector addition of the claim vectors 504. In an example embodiment, aggregating the claim vectors 504 to generate the corresponding entity vector 504 comprises performing an average of the claim vectors 504. In various embodiments, a variety of methods may be used to aggregate the claim vectors 504 associated with a common member or provider identifier to generate an entity vector 506 corresponding to the member or provider. In various embodiments, the entity vectors are stored in corresponding entity profiles (e.g., member profiles stored in member data 212, provider profiles stored in provider data 213) in association with time information/data indicating the time period to which the entity vector corresponds.

In various embodiments, the entity vectors corresponding to a time period may be used to determine behavior signal values corresponding to the time period. Time ordered series of these behavior signal values provide behavior signals that may be monitored and/or analyzed to determine patterns of entity behavior. In various embodiments, clusters of providers and/or members may be identified. For example, geographic clusters corresponding to providers that practice in the same geographic area (e.g., country, region of a country, state, region of a state, county, city, and/or the like) may be identified based at least in part on geographic locations associated with the providers and a corresponding geographic cluster identifier may be stored in association with a provider profile that identifies one or more geographic clusters of which the provider is a part. In another example, providers may be clustered based at least in part on specialties. For instance, the providers may be clustered based at least in part on proclaimed specialties (e.g., association with a professional specialty organization, registration of the provider as a practicing a particular specialty, and/or the like). For example, the provider peer clusters may be identified using a clustering algorithm to identify clusters of entity vectors corresponding to providers. In various embodiments, member geographic clusters and/or member peer clusters may be identified. In various embodiments, the behavior signals include behavior signals that indicate how a provider's behavior changes with respect to a corresponding cluster, how the behavior of a cluster changes over time, how the behavior of a provider changes over time, how the behavior of a member changes with respect to one or more providers, how the behavior of a member changes over time, and/or the like.

FIG. 6 provides a flowchart illustrating various processes, procedures, operations, and/or the like performed (e.g., by an analysis computing entity 65) to generate behavior signals and provide the behavior signals and/or results of analyzing the behavior signals. Starting at step/operation 602, cluster vectors corresponding to a time period are determined. For instance, the analysis computing entity 65 may determine, generate, calculate, and/or the like cluster vectors corresponding to the time period. For example, the analysis computing entity 64 may comprise means, such as processing element 205, memory (e.g., volatile memory 207 and/or non-volatile memory 206), and/or the like, for determining, generating, calculating, and/or the like cluster vectors corresponding to the time period. For instance, a clustering module 222 may be executed by the analysis computing entity 65 to identify, generate, and/or the like one or more provider geographical clusters, member geographical clusters, provider specialty clusters, provider peer clusters, member peer clusters, and/or the like.

In various embodiments, an entity profile corresponding to an entity (e.g., provider or member/patient) is associated with one or more cluster identifiers (e.g., corresponding to geographic clusters, specialty clusters, peer clusters, and/or the like). In some example embodiments, an entity's inclusion in a cluster is static with respect to time (e.g., unchanging) unless a change is made to the entity profile (e.g., a provider is practicing in a new location, a member has moved to a new location, a provider is practicing a different specialty, and/or the like). For example, a clustering algorithm may be used to generate provider peer clusters during one time period and the providers may be assumed to maintain their association with the provider peer cluster through succeeding time periods. In some example embodiments, provider peer clusters (and/or member peer clusters) are determined for each time period (e.g., prior to determining behavior signal values corresponding to the peer clusters for that time period). For instance, as shown in FIG. 7, a plurality of entity vectors 506 (e.g., 506A, 506B; each corresponding to a provider) may be determined (e.g., as described above with respect to FIG. 4, in various embodiments). A clustering algorithm may be used to identify clusters 702 (e.g., 702A, 702B, 702C) from the plurality of entity vectors 506. In an example embodiment, a density-based clustering algorithm is used to identify clusters 702 of entity vectors 506. As should be understood, each entity vector 506 is associated with an entity identifier (e.g., provider identifier or member identifier) that identifies the corresponding entity (e.g., provider or member/patient). Thus, the providers and/or members/patients may each be associated with a peer cluster and the corresponding entity profile may be associated with a peer cluster identifier configured to identify the corresponding peer cluster.

A cluster vector 704 (e.g., 704A, 704B) may be generated by aggregating the entity vectors 506 of the entities in the cluster. For example, a first cluster vector 704A may be generated by aggregating the entity vectors 506 of each of the entities in the first cluster. For instance, each of the entity vectors 506 contained within the dotted line that defines the boundary of the first cluster vector 702A may be aggregated to generate the first cluster vector 704A. In an example embodiment, aggregating the entity vectors 506 to generate the corresponding cluster vector 704 comprises performing a vector addition of the entity vectors 506. In an example embodiment, aggregating the entity vectors 506 to generate the corresponding cluster vector 704 comprises performing an average of the entity vectors 506. In various embodiments, a variety of methods may be used to aggregate the entity vectors 506 associated with a common cluster identifier to generate a cluster vector 704 corresponding to the cluster. In various embodiments, the cluster vectors and associated cluster identifiers are stored (e.g., in non-volatile memory 206) in association with time information/data indicating the time period to which the cluster vector 704 corresponds.

Continuing with FIG. 6, at step/operation 604, behavior signal values corresponding to the time period are determined. For example, the behavior signal values may indicate a relationship between an entity and a cluster and/or two entities at a time period. For instance, the behavior signal values may indicate a change in behavior of an entity over time, change in behavior of a cluster over time, and/or the like corresponding to the time period. For example, the analysis computing entity 65 may determine one or more behavior signal values corresponding to the time period. For instance, the analysis computing entity 65 may comprise means, such as processing element 205, memory (e.g., volatile memory 207 and/or non-volatile memory 206), and/or the like, for determining one or more behavior signal values corresponding to the time period. For example, a signal generation module 224 executing on the analysis computing entity 65 may generate one or more behavior signal values.

For instance, FIG. 8A illustrates a cluster 800 having cluster vector 804 and comprising entity vector 802 at time T=t1 and the same cluster 800 having cluster vector 804 and comprising entity vector 804 at time T=t2, where t1 and t2 indicate different time periods. In an example embodiment, t1 and t2 are immediately adjacent time periods such that time t1 immediately precedes time t2. A provider behavior distance from cluster (e.g., geographic cluster, specialty cluster, and/or peer cluster) may be determined. For example, at time T=t1, the provider behavior distance from cluster is shown by entity-cluster distance 806A and at time T=t2, the provider behavior distance from cluster is shown by entity-cluster distance 806B. In some embodiments, a member-provider behavior signal value (e.g., member behavior distance from an associated provider) may be determined. For instance, the distance between an entity vector corresponding to a member/patient and an entity vector corresponding to a provider (e.g., where a member identifier corresponding to the member/patient and a provider identifier corresponding to the provider are both present in an instance of claim information/data during the time period) may be determined. Some behavior signal values correspond to changes in entity and/or cluster behavior over time (e.g., between time periods, between immediately adjacent time periods, and/or the like). For example, an entity behavior change in time signal value may be determined by determining the scalar and/or vector difference between the vector 808B corresponding to entity vector 802 at time T=t2 and vector 808A corresponding to the entity vector 802 at time T=t1. For instance, a provider behavior change in time signal value may be determined for one or more providers. For example, a member behavior change in time signal value may be determined for one or more members/patients. For instance, a cluster behavior change in time signal value may be determined by determining the scalar and/or vector difference between the vector 810B corresponding to cluster vector 804 at time T=t2 and vector 810A corresponding to the cluster vector 804 at time T=t1. For example, a provider geographical, specialty, and/or peer cluster behavior change in time signal value may be determined for one or more provider geographical, specialty, and/or peer clusters. For instance, FIG. 8B illustrates an example provider behavior signal 850 that illustrates how an example provider's behavior change over time.

Returning to FIG. 6, at step/operation 606, one or more entity profiles (e.g., member and/or provider profiles stored in member data 212 and provider data 213, respectively) and/or cluster profiles may be updated to include the corresponding determined behavior signal values. In various embodiments, the analysis computing entity 65 updates one or more entity profiles (e.g., member and/or provider profiles stored in member data 212 and provider data 213, respectively) and/or cluster profiles to include the corresponding determined behavior signal values. For example, the analysis computing entity 65 may comprise means, such as processing element 205, memory (e.g., volatile memory 207 and/or non-volatile memory 206), and/or the like, for updating one or more entity profiles and/or one or more cluster profiles. For instance, an entity profile and/or a cluster profile may include one or more behavior signal arrays, where each component and/or position of the array is a behavior signal value corresponding to a particular time period. The determined behavior signal values may be added to the corresponding behavior signal arrays in a position corresponding to the time period that corresponds to the instances of claim information/data processed to generate the behavior signal values.

At step/operation 608, one or more behavior signals corresponding to one or more entities and/or one or more clusters may be analyzed to identify behavior patterns, determine suggestions for provider improvement, identify anomalous behavior patterns, determine future behavior predictions, and/or the like. For example, one or more behavior signals may be provided as input to signal processing module 226 (e.g., executing on the analysis computing entity 65) configured to analyze one or more behavior signals to identify behavior patterns, determine suggestions for provider improvement, identify anomalous behavior patterns, determine future behavior predictions, and/or the like. For instance, the analysis computing entity 65 may analyze one or more behavior signals corresponding to one or more entities and/or one or more clusters to identify behavior patterns, determine suggestions for provider improvement, identify anomalous behavior patterns, determine future behavior predictions, and/or the like. For example, the analysis computing entity 65 may comprise means, such as processing element 205, memory (e.g., volatile memory 207 and/or non-volatile memory 206), and/or the like for identifying behavior patterns, determining suggestions for provider improvement, identifying anomalous behavior patterns, determining future behavior predictions, and/or the like. In an example embodiment, one or more providers may be identified within a provider cluster (e.g., geographic cluster, specialty cluster, or peer cluster) whose behavior influences and/or leads the evolution of behavior of the corresponding provider cluster.

For instance, one or more behavior signals and/or external information/data (e.g., information/data corresponding to external factors such as insurance company and/or government policy changes, provider ratings, pricing changes, insurance plan changes, news, events, and/or other happenings that are not governed and/or controlled by a particular entity (e.g., provider or member/patient)) to a machine-learning-based model. For example, the one or more behavior signals and/or external information/data may be provided to a neural network and/or the like trained to identify behavior patterns within a behavior signal, correlations between features of a behavior pattern and features of external information/data, and/or the like. In an example embodiment, the external information/data provided may include prediction external information/data corresponding to one or more time periods that have not yet occurred and one or more predicted behavior signal values may be generated (e.g., corresponding to the one or more time periods that have not yet occurred) based at least in part on the determined and/or identified behavior patterns, correlations, and/or the like.

In an example embodiment, the analysis computing entity 65 may analyze one or more behavior signals, cluster vectors, entity vectors, claims vectors, and/or element vectors corresponding to the time period to identify suggestions that may improve a provider's performance and/or bring an entity vector corresponding to the provider into closer proximity with the corresponding cluster vector. For instance, a first provider may use a first medical code when submitting a claim. Other providers within the same provider peer cluster may use a second medical code, which is similar to the first medical code (e.g., corresponds to a similar diagnosis, procedure, medication, equipment, and/or the like). Thus, the entity vector corresponding to the first provider may be moved closer to the cluster vector of the corresponding provider peer cluster if the first provider used the second medical code instead of the first medical code. It may therefore be determined that the first provider's performance would be improved if the first provider switched to using the second medical code (and the corresponding diagnosis, procedure, medication, equipment, and/or the like) as appropriate within the first provider's practice.

In an example embodiment, anomalous behavior patterns may be identified. For example, the one or more behavior signals may be processed (e.g., by a machine-learning-based model and/or the like executing on the analysis computing entity 65) to identify anomalous behavior patterns. For instance, significant changes in provider's behavior and/or significant change in a provider's behavior with respect to provider geographical cluster, specialty cluster, and/or peer cluster with which the provider is associated may be flagged as anomalous behavior. Similarly, if a member-provider behavior signal for a first member and a first provider is significantly different from other member-provider behavior signals for the first provider, it may be determined that the first member is exhibiting anomalous behavior. In various embodiments, a variety of techniques may be used to identify provider and/or member behavior patterns that are indicative of anomalous behavior.

At step/operation 610, one or more behavior signals and/or results of analyzing one or more behavior signals provided. For example, the analysis computing entity 65 may provide (e.g., transmit) one or more behavior signals and/or results of analyzing one or more behavior signals such that a user computing entity 30 (e.g., insurance company affiliate computing entity, provider computing entity) may receive the one or more behavior signals and/or results of analyzing one or more behavior signals. In various embodiments, the user computing entity 30 may be configured to provide (e.g., via a user interface thereof) an interactive user interface. For instance, the interactive user interface may be provided via an online portal, dashboard provided via a web browser, via a dedicated application, and/or the like. The interactive user interface may display and/or otherwise provide the one or more behavior signals and/or results of analyzing one or more behavior signals.

FIG. 9 illustrates an example dashboard 900 (e.g., displayed via a display 316 of a user computing entity 30). In various embodiments, the dashboard 900 provides a representation of at least some of the instances of claim information/data that was used to generate the behavior signals and the behavior signals and/or result(s) of analyzing behavior signals. In an example embodiment, the behavior signals track the pairwise position over time between entity vectors corresponding to providers and/or members/patients and/or between entity vectors corresponding to providers and/or members/patients and cluster vectors for corresponding clusters.

In an example embodiment, the dashboard 900 comprises a claims data summary 902. For example, the claims data summary 902 may provide a summary of a group of instances of claim information/data that was analyzed to provide the behavior signals. For instance, the claims data summary 902 may provide a summary of the instances of claim information/data corresponding to the current and/or most recent time period. For example, the claims data summary 902 may indicate the number of providers and/or number of members represented in the instances of claim information/data, the number of claims represented by the instances of claim information/data, amount paid responsive to processing the claims represented by the instances of claim information/data, and/or the like. In an example embodiment, the dashboard 900 may comprise a provider peer cluster behavior distance section 904 that illustrates the relative size of provider peer clusters and the amount paid to each provider peer cluster. In an example embodiment, the dashboard 900 may comprise a behavior trend section 906 that may illustrate one or more trends identified in various behavior signals. In an example embodiment, the dashboard 900 may comprise a provider behavior distance with respect to peer cluster section 908 that illustrates the distance an entity vector corresponding to a provider is from the cluster vector of a corresponding cluster. In an example embodiment, the provider behavior distance with respect to peer cluster section 908 illustrates one or more medical codes used by one or more providers and suggestions for codes that the one or more providers could switch to to cause the provider's behavior distance with respect to the peer cluster to be reduced. In an example embodiment, the dashboard 900 may comprise a selected provider/cluster indicator 910. In an example embodiment, various aspects of the dashboard 900 may be broken down by geographic location. Various components of the illustrated dashboard 900 may be swapped with various other graphical representations of various behavior signals and/or results of analyzing the behavior signals, in various embodiments.

FIG. 10 illustrates a prediction dashboard view 1000 of the dashboard 900 displayed as an interactive user interface via the user interface of a user computing entity 30. For instance, a model (e.g., machine-learning-based model) may be used to model a behavior signal. Based at least in part on external information/data (e.g., information/data corresponding to external factors such as insurance company and/or government policy changes, provider ratings, pricing changes, insurance plan changes, news, events, and/or other happenings that are not governed and/or controlled by a particular entity (e.g., provider or member/patient)) provided to the model. Based at least in part on the modeled behavior signal and the external information/data, the model may predict future signal values for the behavior signal. The predicted future signal values may be provided through the prediction dashboard view 1000.

In various embodiments, a variety of other dashboard views may be available for user review. For example, the dashboard may be configured to provide various behavior signals and/or results of analyzing the behavior signals via an interactive user interface provided via the user interface of a user computing entity 30.

V. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for tracking entity behavior over time, the method comprising:
   receiving, by an analysis computing entity, one or more instances of claim data, wherein each instance of claim data corresponds to an entity and comprises one or more features;
   generating, by the analysis computing entity, a claim vector for each instance of claim data based at least in part on the one or more features of the one or more instances of claim data, wherein each claim vector is generated by one or more machine learning models;
   adding, by the analysis computing entity, the claim vector to a group of claim vectors, wherein each claim vector within the group of claim vectors corresponds to a same corresponding entity;
   generating, by the analysis computing entity and for the group of claim vectors, an entity vector corresponding to the corresponding entity, wherein the entity vector is generated by the one or more machine learning models;
   based at least in part on the entity vector and at least one of (a) an entity profile corresponding to the corresponding entity or (b) an entity cluster with which the corresponding entity is associated, determining, by the analysis computing entity, at least one behavior signal value for the corresponding entity;
   updating, by the analysis computing entity, a behavior signal to include the at least one behavior signal value, wherein the behavior signal (a) is stored in a data structure, (b) comprises at least two behavior signal values, and (c) each of the at least two behavior signal values is associated with a time period; and
   providing, by the analysis computing entity, the behavior signal for at least one of (a) display via an interactive user interface of a user computing entity or (b) further processing for pattern identification and/or behavior prediction.

2. The method of claim 1, wherein the entity is a healthcare provider or a member of an insurance policy.

3. The method of claim 1, wherein generating the claim vector comprises generating element vectors corresponding to elements of the one or more features of the one or more instances of claim data.

4. The method of claim 1, wherein the entity cluster is identified using density-based clustering analysis of a plurality of entity vectors.

5. The method of claim 1, wherein the entity cluster is one of a provider geographic cluster, a provider specialty cluster, or a provider peer cluster.

6. The method of claim 1, wherein the further processing comprises detection of anomalous behavior.

7. The method of claim 1, wherein the behavior prediction is performed based at least in part on external information corresponding to external factors.

8. The method of claim 1, wherein the at least one behavior signal value is (a) a provider behavior distance from provider peer cluster, (b) a provider behavior distance from provider specialty cluster, (c) a member behavior distance from provider, (d) a provider behavior distance from a treatment, (e) a change of provider behavior with time, (f) a change in peer cluster behavior with time, (g) a change in specialty cluster behavior with time, or (h) a change of member behavior with time.

9. An apparatus comprising at least one processor, at least one communications interface, and at least one memory including computer program code, the computer program code comprising executable instructions, the at least one memory and computer program code configured to, with the processor, cause the apparatus to at least:
   receive, by at least the processor, one or more instances of claim data, wherein each instance of claim data corresponds to an entity and comprises one or more features;
   generate a claim vector for each instance of claim data based at least in part on the one or more features of the one or more instances of claim data, wherein each claim vector is generated by one or more machine learning models;
   add the claim vector to a group of claim vectors, wherein each claim vector within the group of claim vectors corresponds to a same corresponding entity;
   generate, for the group of claim vectors, an entity vector corresponding to the corresponding entity, wherein the entity vector is generated by the one or more machine learning models;
   based at least in part on the entity vector and at least one of (a) an entity profile corresponding to the corresponding entity or (b) an entity cluster with which the corresponding entity is associated, determine at least one behavior signal value for the corresponding entity;
   update a behavior signal to include the at least one behavior signal value, wherein the behavior signal (a) is stored in a data structure, (b) comprises at least two behavior signal values, and (c) each of the at least two behavior signal values is associated with a time period;
   and provide the behavior signal for at least one of (a) display via an interactive user interface of a user computing entity or (b) further processing for pattern identification and/or behavior prediction.

10. The apparatus of claim 9, wherein the entity is a healthcare provider or a member of an insurance policy.

11. The apparatus of claim 9, wherein generating the claim vector comprises generating element vectors corresponding to elements of the one or more features of the one or more instances of claim data.

12. The apparatus of claim 9, wherein the entity cluster is identified using density-based clustering analysis of a plurality of entity vectors.

13. The apparatus of claim 9, wherein the entity cluster is one of a provider geographic cluster, a provider specialty cluster, or a provider peer cluster.

14. The apparatus of claim 9, wherein the further processing comprises detection of anomalous behavior.

15. The apparatus of claim 9, wherein the behavior prediction is performed based at least in part on external information corresponding to external factors.

16. The apparatus of claim 9, wherein the at least one behavior signal value is (a) a provider behavior distance from provider peer cluster, (b) a provider behavior distance from provider specialty cluster, (c) a member behavior distance from provider, (d) a provider behavior distance from a treatment, (e) a change of provider behavior with time, (f) a change in peer cluster behavior with time, (g) a change in specialty cluster behavior with time, or (h) a change of member behavior with time.

17. A computer program product comprising at least one non-transitory computer-readable storage medium having computer-executable program code portions stored therein, the computer-executable program code portions comprising program code instructions, the computer program code instructions, when executed by a processor of a computing entity, are configured to cause the computing entity to:

receive one or more instances of claim data, wherein each instance of claim data corresponds to an entity and comprises one or more features;

generate a claim vector for each instance of claim data based at least in part on the one or more features of the one or more instances of claim data, wherein each claim vector is generated by one or more machine learning models;

add the claim vector to a group of claim vectors, wherein each claim vector within the group of claim vectors corresponds to a same corresponding entity;

generate, for the group of claim vectors, an entity vector corresponding to the corresponding entity, wherein the entity vector is generated by the one or more machine learning models;

based at least in part on the entity vector and at least one of (a) an entity profile corresponding to the corresponding entity or (b) an entity cluster with which the corresponding entity is associated, determine at least one behavior signal value for the corresponding entity;

update a behavior signal to include the at least one behavior signal value, wherein the behavior signal (a) is stored in a data structure, (b) comprises at least two behavior signal values, and (c) each of the at least two behavior signal values is associated with a time period; and provide the behavior signal for at least one of (a) display via an interactive user interface of a user computing entity or (b) further processing for pattern identification and/or behavior prediction.

18. The computer program product of claim 17, wherein the at least one behavior signal value is (a) a provider behavior distance from provider peer cluster, (b) a provider behavior distance from provider specialty cluster, (c) a member behavior distance from provider, (d) a provider behavior distance from a treatment, (e) a change of provider behavior with time, (f) a change in peer cluster behavior with time, (g) a change in specialty cluster behavior with time, or (h) a change of member behavior with time.

\* \* \* \* \*